United States Patent [19]
Totani et al.

[11] Patent Number: 4,658,048
[45] Date of Patent: Apr. 14, 1987

[54] PLATINUM COMPLEXES

[75] Inventors: Tetsushi Totani; Osamu Shiratori, both of Hyogo; Katsutoshi Aono; Naomi Uchida, both of Nara, all of Japan

[73] Assignee: Shionogi & Co., Ltd., Osaka, Japan

[21] Appl. No.: 741,890

[22] Filed: Jun. 6, 1985

[30] Foreign Application Priority Data

Jun. 20, 1984 [JP] Japan .................. 59-126845

[51] Int. Cl.4 .................. A01N 55/02; A61K 31/28; C07F 15/00
[52] U.S. Cl. .................. 556/137; 556/137
[58] Field of Search .................. 556/137; 514/492

[56] References Cited

U.S. PATENT DOCUMENTS 4,271,085 6/1981 Amundsen et al. .................. 556/137
4,359,425 11/1982 Totani et al. .................. 556/137
4,560,781 12/1985 Totani et al. .................. 556/137
4,575,550 3/1986 Totani .................. 556/137 X
4,577,038 3/1986 Totani et al. .................. 556/137

OTHER PUBLICATIONS

Chemical Abstracts 97 207122q (1982).

Primary Examiner—Helen M. S. Sneed
Attorney, Agent, or Firm—Wenderoth, Lind & Ponack

[57] ABSTRACT

Novel platinum (IV) complexes having potent antitumor and antibacterial activities and high water solubility with low toxicity and pharmaceutical and/or veterinarily compositions containing one or more compounds together with one or more carriers are provided.

They can be prepared by reacting a corresponding platinum (II) complex with hydrogen peroxide or halogen.

15 Claims, No Drawings

PLATINUM COMPLEXES

BACKGROUND OF THE INVENTION

1. Field of the Invention

The present invention relates to novel platinum complexes which show potent antibacterial and/or antitumor activities with low toxicity.

2. Prior Art

Compounds analogous to cisplatin [Bristol Myers Co.] and their mechanism of pharmacological action have been investigated since antitumor activity of cisplatin was observed. In fact many platinum complexes such as malonato(1,2-diaminocyclohexane)-platinum-(II) [U.S. Pat. No. 4,169,846], cis-dichloro-transdihydroxy-bis(isopropylamine)platinum(IV) [U.S. Pat. No. 4,394,319], and the like are known presently.

The present inventors have investigated to develop platinum complexes analogous to cisplatin from the early stage of study and prepared novel platinum complexes described in European Pat. No. 0057023, British Pat. Pub. Nos. 2132201A, 2140804A, JPN Unexamd. Pat. Pub. No. 59-222497, and the like.

Problems in the prior art will be illustratively explained. Cisplatin has the following problems.

(i) It can not be administered easily because of its low water- and fat- solubility, whereby its utility is limited.

(ii) Toxicity, particularly nephrotoxicity is high.

The present inventors have studied to improve the solubility of the compounds of the present invention in order that the compounds can be administered easily. They also have studied to reduce the toxicity and increase the activities.

As the result of the studies, they have succeeded in preparing novel platinum(IV) complexes which have a bidentate ligand of the formula:

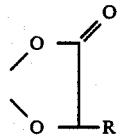

(wherein R is hydrogen, phenyl, or optionally substituted lower alkyl), N-base donors as monodentate ligands (e.g., amine, primary amine) or bidentate ligand such as a diamine, and two monodentate ligands.

The alphabets a~f are utilized for indicating the relative configuration of each ligand in three dimensions.

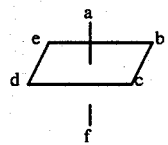

BRIEF SUMMARY OF THE INVENTION

The present invention relates to platinum(IV) complexes. More particularly, it relates to a compound of the formula (I):

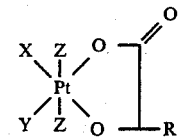

wherein R is hydrogen, phenyl, or optionally substituted lower alkyl; X and Y each is amine or lower alkylamine; or X and Y taken together form ethane-1,2-diamine, cyclohexane-1,2-diamine, bicyclo[2.2.1]heptane-2,3-diamine, adamantane-1,2-diamine, cyclohexane-1,1-bis(methylamine), or cyclohexane-2-amine-1-methylamine; and Z is halogen, hydroxy, or an alkali-metal salt of hydroxy; and a composition comprising one or more said compounds and one or more carriers.

The compounds (I) can be prepared by reacting a compound of the formula (II):

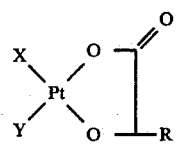

(wherein R, X, and Y each has the same meaning as defined above) with hydrogen peroxide or halogen.

The compounds (I) are useful as parenterally administrable antibacterial and/or antitumor agents.

DETAILED DESCRIPTION OF THE INVENTION

The present invention relates to platinum(IV) complexes. More particularly, it relates to a compound of the formula (I):

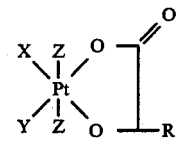

wherein R is hydrogen, phenyl, or optionally substituted lower alkyl; X and Y each is ammine or lower alkylamine; or X and Y taken together form ethane-1,2-diamine, cyclohexane-1,2-diamine, bicyclo[2.2.1]heptane-2,3-diamine, adamantane-1,2-diamine, cyclohexane-1,1-bis(methylamine), or cyclohexane-2-amine-1-methylamine; and Z is halogen, hydroxy, or an alkali-metal salt of hydroxy; and a composition comprising one or more said compounds and one or more carriers.

In the above definition relative to R, X, Y, and Z, the optionally substituted lower alkyl means substituted or unsubstituted $C_1$–$C_6$ alkyl, the $C_1$–$C_6$ alkyl includes methyl, ethyl, n-propyl, isopropyl, n-butyl, isobutyl, sec-butyl, tert-butyl, n-pentyl, isopentyl, sec-pentyl, neo-pentyl, n-hexyl, isohexyl, sec-hexyl, and the like and representatives of substituents on the $C_1$–$C_6$ alkyl are hydroxy, halogen (e.g., fluorine, chlorine, bromine, iodine, etc.) and the like; the substituted $C_1$–$C_6$ alkyl includes hydroxy-lower alkyl and halogeno-lower alkyl. The lower alkylamine means $C_1$–$C_6$ alkylamine, for example methylamine, ethylamine, n-propylamine, isopropylamine, n-butylamine, isobutylamine, sec-butylamine, tert-butylamine, n-pentylamine, isopentylamine, neo-pentylamine, tert-pentylamine, and the like. The halogen includes fluorine, chlorine, bromine, iodine, and the like. In the alkali-metal salt of hydroxy, the alkali-metal salt is exemplified by lithium salt, sodium salt, potassium salt, and the like.

The objective compounds (I) of the present invention can be prepared easily according to the following methods (i) and (ii). (i) When Z is halogen.

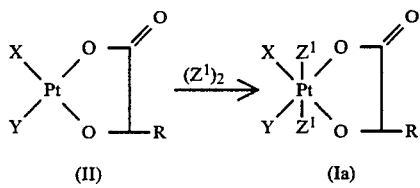

[wherein $Z^1$ is halogen (fluorine, chlorine, bromine, iodine, etc.); R, X, and Y each has the same meaning as defined above].

The compound (I) wherein Z is halogen, namely the compound (Ia) may be prepared in accordance with the reaction sequence described above.

The compound (II) may be allowed to react with halogen in an aqueous medium at room temperature or an elevated temperature under heating, for example 15° to 100° C.

The halogen used in the reaction may be used in an equivalent amount to the compound (II); chlorine is used as an aqueous solution, bromine as liquid form, and iodine as solid form.

(ii) When Z is hydroxy or alkali-metal salt of hydroxy.

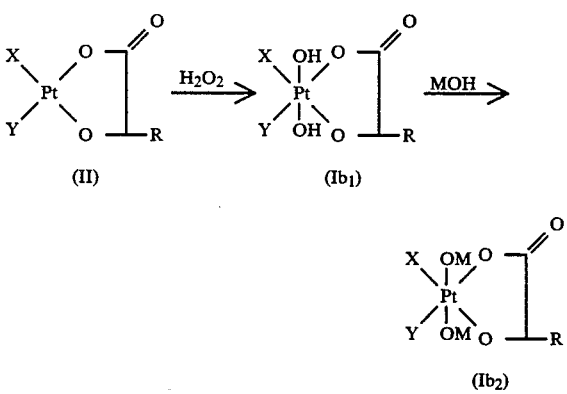

[wherein M is alkali metal (lithium, sodium, potassium, etc.); R, X, and Y each has the same meaning as defined above.]

The compound (I) wherein Z is hydroxy or alkali-metal salt of hydroxy (i.e., the compound (Ib₁) or (Ib₂)) can be prepared according to the reaction sequence as described above.

The compound (II) may be allowed to react with hydrogen peroxide in an aqueous medium at room temperature or an elevated temperature up to 100° C. to give the objective compound (Ib₁). The hydrogen peroxide may preferably be used in an amount of 2 mol equivalents to the compound (II).

Subsquently, the compound (Ib₁) may be allowed to react with about 2 equimolar amount of alkali metal hydroxide in an aqueous medium to give the objective compound (Ib₂). The reaction may be carried out at room temperature or an elevated temperature up to 120° C. and it terminates within a period of several hours.

The alkali metal hydroxide includes lithium hydroxide, sodium hydroxide, potassium hydroxide, and the like.

The starting compounds (II) in the above reaction sequence can be obtained in the same manner as described in the specifications British Pat. Pub. Nos. 2132201A and 2140804A according to the following reaction sequence.

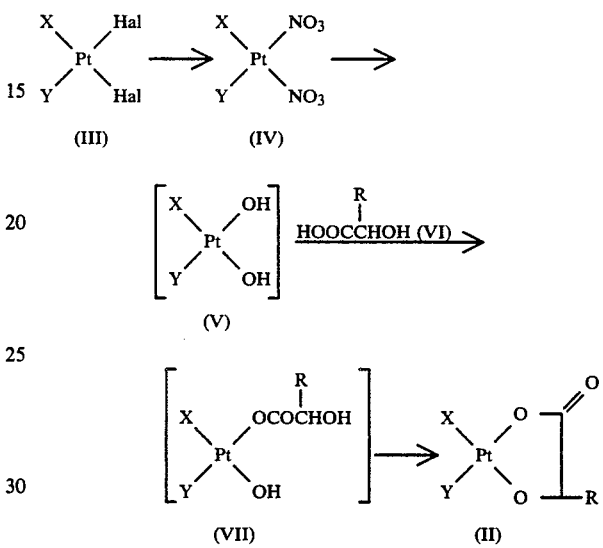

[wherein Hal is halogen (chlorine, bromine, iodine, etc.); R, X, and Y each has the same meaning as defined above].

The compounds (III) are known; and the compounds (IV) are known or may be prepared by reacting the compounds (III) with silver nitrate.

In the reaction sequence described above, an aqueous solution of the compound (IV) is passed through a column of anion exchange resin (OH—type) such as Amberlite IRA-400 (Rohm & Haas Co.), Dowex I (Dow Chemical Co.), or Daiaion SA-10A (Mitsubishi Chemical Industries Ltd.) to give the compound (V) as main product in which the two nitrato groups are replaced by hydroxy groups. Preferably, the resulting compound (V) is usually used in the next step in a form of a solution separated above since this compound is unstable in solid form.

The compound (V) is allowed to react with α-hydroxy acid (VI) in an aqueous medium to give the desired compound (II) of the present invention, probably through the intermediate (VII). The reaction of the compound (IV) to produce the compound (V) proceeds quantitatively, so α-hydroxy acid (VI) may be used in an equivalent amount to the compound (IV). The present reaction is usually carried out at room temperature and terminates within 10 days; if necessary the reaction may be conducted at an elevated temperature of, for example, 50° to 70° C.

The compounds of the present invention have antibacterial activity; and they have antitumor activity comparable to or more potent than that of cisplatin with lower nephrotoxicity. Furthermore, they can easily be administered parenterally since they are highly soluble in water. Thus, for example, the compounds (I) may be dissolved or suspended in appropriate solvents for injection (e.g., distilled water for injection, physiological saline, 5% aqueous glucose, 5% aqueous mannitol, aqueous ethanol, aqueous glycerin, and aqueous propylene glycol), and can be administered intravenously, intramuscularly, or subcutaneously, or by means of instillation. The compounds (I) may be placed in sealed ampoules as solutions or suspensions, or more preferably preserved in ampoules or vials in solid forms, e.g., crystals, powders, fine crystals, or lyophilizates suitable to be dissolved immediately before the treatment. Stabilizer may also be added.

The present invention includes a pharmaceutical or veterinary formulation comprising a compound of the present invention. Such formulations may contain one or more usual carriers, diluents, or excipients.

Minimum inhibitory concentration (MIC) (μg/ml) of (trans-dichloro)(glycolato-O,O')(diammine)platinum-(IV) against Pseudomonas aeruginosa in vitro was 25.0 (μg/ml).

The compounds (I) can be administered to human adults at a dose or doses of 20 to 2000 mg/day in the treatment of infectious disease.

The objective compounds (I) of the present invention have higher water-solubility than other platinum complexes have and show potent antitumor activities; particularly the compounds (I) show outstanding antitumor activities against solid cancers with low nephrotoxicity.

When the compounds (I) are used in the treatment of human tumors, they are parenterally administered to an adult patient at a dose or doses of 100 to 2000 mg/day, usually 1 to 3 times a day.

The antitumor activity of the objective compounds (I) of the present invention will be explained by the following Experiment.

EXPERIMENT

Antitumor activity against Walker carcinosarcoma 256

Tumor seed of Walker carcinosarcoma 256 was subcutaneously inoculated to Wister rats (5 weeks of the age, female) and a predetermined amount of the test compound was intravenously administered for 5 days continuously from the next day of the inoculation. Saline was used as vehicle for injection.

Test compounds (A) (trans-Dihydroxo)(glycolato-O,O')(diammine)-platinum(IV) 2
(B) (trans-Dichloro)(glycolato-O,O')(diammine)-platinum(IV) 3
(C) (trans-Dihydroxo)(glycolato-O,O')(ethane-1,2-diamine)platinum(IV) 17
(D) (trans-Dihydroxo)(glycolato-O,O')(trans-1-cyclohexane-1,2-diamine)platinum(IV) 33
(E) cis-Dichlorodiammineplatinum(II) (generic name: Cisplatin, Control)

Evaluation of Effect

From the average survival days (a) in each test group and those (b) of the untreated control group, the increase of lifespan (ILS) was calculated according to the following formula.

$$ILS (\%) = \frac{(a) - (b)}{(b)} \times 100$$

An effect was evaluated from a dosage showing 30% increase of lifespan: $ILS_{30}$, dosage showing maximum increase of lifespan: $ILS_{max}$, and a curative index: CI.

$$CI = \frac{ILS_{MAX}}{ILS_{30}}$$

The larger the CI value is, the more effective the compound is.

| | Compound (A) 2 | | |
|---|---|---|---|
| Dose (mg/kg) | Number of rats employed | ILS (%) | Number of rats survived more than 60 days |
| 0 × 5 | 10 | — | 0 |
| 1.25 × 5 | 6 | 65 | 0 |
| 2.5 × 5 | 6 | >211 | 1 |
| 5 × 5 | 6 | >417 | 6 |
| 10 × 5 | 6 | >417 | 6 |
| 20 × 5 | 6 | >417 | 6 |
| 40 × 5 | 6 | >417 | 6 |
| 80 × 5 | 6 | −50 | 0 |

Dose (mg/kg) = (mg/kg/day) × (day)
(0 × 5) means the dose administered to control group.

| | Compound (B) 3 | | |
|---|---|---|---|
| Dose (mg/kg) | Number of rats employed | ILS (%) | Number of rats survived more than 60 days |
| 0 × 5 | 10 | | |
| 0.625 × 5 | 6 | 13 | |
| 1.25 × 5 | 6 | 44 | |
| 2.5 × 5 | 6 | >352 | 4 |
| 5 × 5 | 6 | >407 | 5 |
| 10 × 5 | 6 | >406 | 4 |
| 20 × 5 | 6 | 26 | |

| | Compound (C) 17 | | |
|---|---|---|---|
| Dose (mg/kg) | Number of rats employed | ILS (%) | Number of rats survived more than 60 days |
| 0 × 5 | 10 | | |
| 1.25 × 5 | 6 | 26 | |
| 2.5 × 5 | 6 | 50 | |
| 5 × 5 | 6 | >312 | 4 |
| 10 × 5 | 6 | >417 | 6 |
| 20 × 5 | 6 | >417 | 6 |
| 40 × 5 | 6 | >417 | 6 |
| 80 × 5 | 6 | >341 | 5 |
| 160 × 5 | 6 | −34 | |

| | Compound (D) 33 | | |
|---|---|---|---|
| Dose (mg/kg) | Number of rats employed | ILS (%) | Number of rats survived more than 60 days |
| 0 × 5 | 10 | | |
| 1.25 × 5 | 6 | 24 | |
| 2.5 × 5 | 6 | 41 | |
| 5 × 5 | 6 | >225 | 2 |
| 10 × 5 | 6 | >394 | 5 |
| 20 × 5 | 6 | >417 | 6 |
| 40 × 5 | 6 | 183 | |
| 80 × 5 | 6 | 177 | |
| 160 × 5 | 6 | 53 | |

| | Compound (E) Cisplatin (control) | | |
|---|---|---|---|
| Dose (mg/kg) | Number of rats employed | ILS (%) | Number of rats survived more than 60 days |
| 0 × 5 | 10 | | |

-continued

| | Compound (E) Cisplatin (control) | | |
|---|---|---|---|
| Dose (mg/kg) | Number of rats employed | ILS (%) | Number of rats survived more than 60 days |
| 0.175 × 5 | 6 | 11 | |
| 0.35 × 5 | 6 | 44 | |
| 0.7 × 5 | 6 | 230 | |
| 1.4 × 5 | 6 | >379 | 4 |
| 2.8 × 5 | 6 | −10 | |

$ILS_{30}$, $ILS_{MAX}$, and CI of the each compounds (A) to (E) are shown in the following table.

| Compounds | (A) | (B) | (C) | (D) | (E) |
|---|---|---|---|---|---|
| $ILS_{30}$ (mg/kg) | 4.8 | 4.2 | 7 | 8 | 1.3 |
| $ILS_{MAX}$ (mg/kg) | 200 | 50 | 200 | 100 | 7 |
| CI | 41.7 | 11.9 | 28.6 | 12.5 | 5.4 |

CI values of the compounds (A)–(D) are about 2 to 8 times larger than that of cisplatin (E), and so the compounds of the present invention are more effective than cisplatin.

The present invention will be explained in more detail by the following examples.

EXAMPLE 1

(trans-Dihydroxo)(glycolato-O,O')(diammine)-platinum(IV) 2

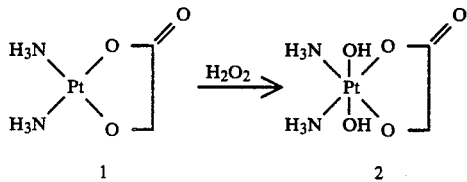

To an aqueous solution (70 ml) of 2.2 g (7.26 mmol) of (glycolato-O,O')(diammine)platinum(II) 1 was added 5.2 g of 10% aqueous hydrogen peroxide and the mixture was allowed to stand at room temperature for 1 hour, concentrated to 8 ml, and ice-cooled. The resulting solid material was collected by filtration and recrystallized from hot water to give 2.2 g of the titled compound 2 monohydrate as slightly yellowish crystals.

m.p.: 190° C. ~(decomp.).

Anal. Calcd. (%) [for $C_2H_{10}N_2O_5Pt(H_2O)_{1.0}$]: C, 6.76; H, 3.41; N, 7.89; Pt, 54.92; $H_2O$, 5.07. Found (%): C, 6.72; H, 3.36; N, 7.86; Pt, 53.89; $H_2O$, 4.82.

IR: $\nu_{max}$(Nujol) 3460(m), 3180(m), 1660(s), 1640(sh), 1570(m), 1430(m), 1325(m), 1295(m), 1050(m), 940(w), 910(m), 755(m), 710(w) cm$^{-1}$.

$^1$HNMR: (in $D_2O$, ppm from TMS as external standard, δ): 4.78(glycolato $CH_2$, $J_{195Pt-H}$=21 Hz).

EXAMPLE 2

(trans-Dichloro)(glycolato-O,O')(diammine)platinum-(IV) 3

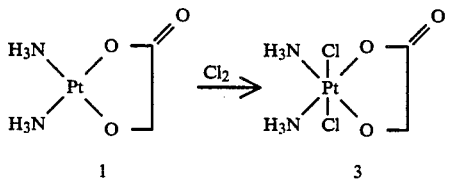

To an aqueous solution (60 ml) of 2.0 g (6.60 mmol) of (glycolato-O,O')(diammine)platinum(II) 1 were aspirated gaseous chlorine for 5 minutes and then air for 10 minutes at room temperature. The yellowish precipitating material was collected by filtration and recrystallized from hot water to give 0.52 g of the titled compound 3 monohydrate as yellow crystals.

Yield: 20%.

m.p.: 115° C. (decomp.)

Anal. Calcd. (%) [for $C_2H_8N_2O_3Cl_2Pt(H_2O)_{1.0}$]: C, 6.13; H, 2.57; N, 7.14; Cl, 18.08; Pt, 49.75; $H_2O$, 4.60. Found (%): C, 6.04; H, 2.41; N, 7.33; Cl, 17.51; Pt, 50.62; $H_2O$, 5.06.

IR: $\nu_{max}$(Nujol) 3570(m), 3360(m), 3245(s), 3175(sh), 1650(s), 1620(sh), 1570(s), 1360(m), 1330(s), 1300(s), 1230(w), 1040(sh), 1035(m), 910(m), 880(w), 755(m), 710(w) cm$^{-1}$. $^1$HNMR: (in $D_2O$, ppm from TMS as external standard, δ) 4.71 (glycolato $CH_2$, $J_{195Pt-H}$=18 Hz).

EXAMPLE 3

(trans-Dihydroxo)(lactato-O,O')(diammine)-platinum(VI) 5

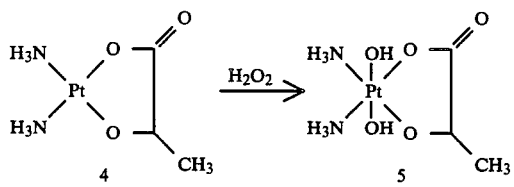

To a mixture of 1.27 g (4.00 mmol) of (lactato-O,O')-(diammine)platinum(II) 4 and 20 ml of water was added 1 ml (8.4 mmol) of 30% aqueous hydrogen peroxide. The mixture was stirred at room temperature for 2 hours and concentrated under reduced pressure at a temperature lower than 35° C. The resulting residue was purifed by silica-gel chromatography to give 0.78 g of the titled compound 5 as 0.6 mol hydrate.

Yield: 54%.

m.p.: 200° C. ~(decomp.)

Anal. Calcd. (%) [for $C_3H_{12}N_2O_5Pt(H_2O)_{0.6}$]: C, 9.95; H, 3.68; N, 7.74; Pt, 53.89. Found (%): C, 9.86; H, 3.69; N, 7.68; Pt, 53.68.

IR: $\nu_{max}$(Nujol) 3600–3350(br), 3350–3000(br), 1650(s), 1340(sh), 1298(m), 1175(w), 1110(m), 1040(m), 920(w), 865(m), 780(w), 723(w) cm$^{-1}$.

$^1$HNMR: (in $D_2O$, ppm from TMS as external standard TMS, δ) 1.92(d, —$CH_3$), 5.08(q, —CH, J=7 Hz).

EXAMPLE 4

(trans-Dibromo)(lactato-O,O')(diammine)platinum (IV) 6

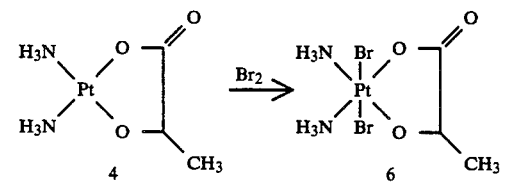

To an aqueous solution (5 ml) of 0.313 g (0.99 mmol) of (lactato-O,O')(diammine)platinum (II) 4 was added 0.16 g (1.0 mmol) of bromine. The mixture was stirred at room temperature for 2 hours, concentrated under reduced pressure at a temperature below 40° C., and the resulting residue was dried under reduced pressure to give 0.42 g of the titled compound 6 as orange crystalline solid.

Yield: 86%.

m.p.: 180°–190° C. (decomp.)

Anal. Calcd. (%) [for $C_3H_{10}N_2O_3Br_2Pt(H_2O)_{1.0}$]: C, 7.28; H, 2.44; N, 5.66; Br, 32.27; Pt, 39.40. Found (%): C, 7.52; H, 2.32; N, 5.78; Br, 31.83; Pt, 39.88.

IR: $\nu_{max}$(Nujol) ~3450(br), 3300–3000(br), 1623(s), 1320(sh), 1276(s), 1095(m), 1035(s), 905(w), 860(m), 780(w), 720(w) cm$^{-1}$.

$^1$HNMR: (in $D_2O$, ppm from TMS as external standard TMS, $\delta$) 1.90(d, —CH$_3$), 5.17(q, —CH, J=8 Hz).

EXAMPLE 5

(trans-Diiodo)(lactato-O,O')(diammine)platinum(IV) 7

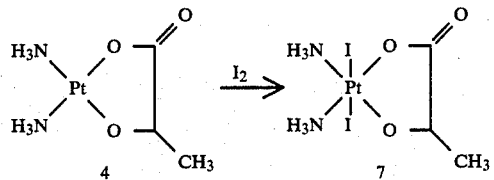

To an aqueous solution (5 ml) of 0.317 g (1.00 mmol) of (lactato-O,O')(diammine)platinum(II) 4 was added 0.254 g (1.00 mmol) of pulverized iodine. The mixture was stirred at room temperature for 2 hours and filtered. The resulting material was washed with water and dried under reduced pressure to give 0.427 g of the titled compound 7. The filtrate and the washed liquid were gathered and concentrated to give further 55 mg of the titled compound 7. Total amount of 7: 0.482 g (yield: 81%).

Appearance: black-brownish crystalline solid.

m.p.: 100° C. ~(decomp.)

Anal. Calcd. (%) [for $C_3H_{10}N_2O_3I_2Pt(H_2O)_{2.0}$]: C, 5.93; H, 2.32; N, 4.61; I, 41.81; Pt, 32.14. Found (%): C, 5.81; H, 2.22; N, 4.71; I, 43.33; Pt, 32.07.

IR: $\nu_{max}$(Nujol) 3600–3000(br), 1600(br), 1370(s), 1343(sh), 1285(m), 1106(m), 1090(sh), 1038(s), 925(w), 865(m), 780(w), 720(w) cm$^{-1}$.

EXAMPLE 6

(trans-Dihydroxo)($\beta$-chlorolactato-O,O')(diammine)platinum (IV) 9

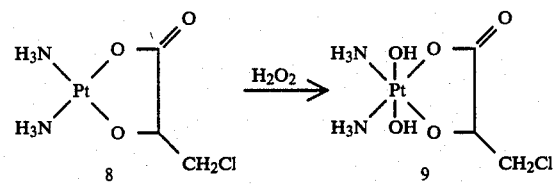

($\beta$-Chlorolactato-O,O')(diammine)platinum(II) 8 (1.55 g, 4.41 mmol) was dissolved in 115 ml of water with heating at 55° C. To the mixture was added 3.8 ml (11.17 mmol) of 10% aqueous hydrogen peroxide. The resulting mixture was concentrated under reduced pressure, and the precipitating white crystalline material was collected by filtration and recrystallized from water to give 0.916 g (yield: 51.5%) of the titled compound as monohydrate.

m.p.: 155° C. ~(decomp.).

Anal. Calcd. (%) [for $C_3H_{11}N_2O_5ClPt(H_2O)_{1.0}$]: C, 8.93; H, 3.25; N, 6.94; Cl, 8.78; Pt, 48.33. Found (%): C, 8.92; H, 3.35; N, 6.94; Cl, 8.96; Pt, 48.18.

IR: $\nu_{max}$(Nujol) 3490(sh), 3450(s), 3250(br), 3050(sh), 1655(s), 1605(w), 1570(sh), 1560(m), 1420(m), 1400(m), 1355(s), 1295(w), 1280(m), 1255(m), 1185(w), 1085(s), 1050(m), 1000(w), 960(w), 910(m), 875(m), 820(m), 685(s), 670(w) cm$^{-1}$.

$^1$HNMR: (in $D_2O$, ppm from TMS as external standard TMS, $\delta$) 4.26(d, J=12 Hz, CH$_2$), 5.37(lactato CH).

EXAMPLE 7

(trans-Dihydroxo)(mandelato-O,O')(diammine)platinum(IV) 11

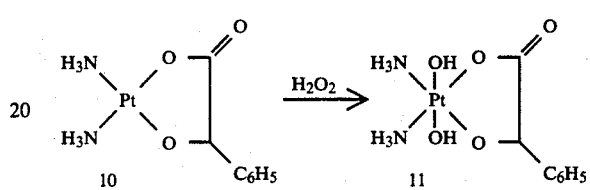

To an aqueous solution (40 ml) of 2 g (5.33 mmol) of (mandelato-O,O')(diammine)platinum(II) 10 was added 1.25 g (11 mmol) of 30% aqueous hydrogen peroxide. The mixture was stirred at room temperature for 2 hours and concentrated at a temperature lower than 35° C.; the resulting residue was dried under reduced pressure to give the titled compound 11.

Anal. Calcd. (%) [for $C_8H_{14}N_2O_5Pt(H_2O)_{2.0}$]: C, 21.38; H, 4.04; N, 6.23; Pt, 43.42. Found (%): C, 22.90; H, 3.73; N, 5.94; Pt, 42.70.

IR: $\nu_{max}$(Nujol) 3600–3330(br,m), 3330–3000(br, m), 1680(s), 1595(sh), 1305(s), 1250(m), 1045(m), 1020(m), 945(m), 820(w), 700(w) cm$^{-1}$.

$^1$HNMR: (in $D_2O$, ppm from TMS as external standard TMS, $\delta$), 5.98(s, mandelato CH, $J_{195Pt-H}$=5.0 Hz), 7.95(s, $C_6H_5$).

EXAMPLE 8

(trans-Dihydroxo)(glycolato-O,O')bis(methylamine)platinum (IV) 13

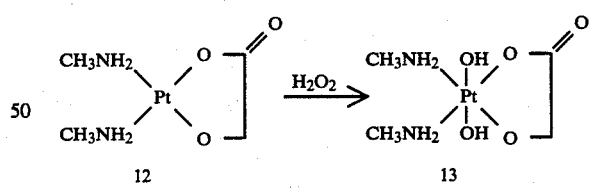

To an aqueous solution (10 m) of 0.99 g (3.00 mmol) of (glycolato-O,O')bis(methylamine)platinum(II) 12 was added 2.2 g (6.45 mmol) of 10% aqueous hydrogen peroxide. The mixture was allowed to stand at room temperature for 1 hour, concentrated under reduced pressure, and dried up. Recrystallized from methanol to give 0.79 g of the titled compound 13.

Yield: 72%.

m.p.: 200° C. ~(decomp.).

Anal. Calcd. (%) [for $C_4H_{14}N_2O_5Pt$]: C, 13.15; H, 3.86; N, 7.67; Pt, 53.42. Found (%): C, 12.88; H, 3.73; N, 7.67; Pt, 52.70.

IR: $\nu_{max}$(Nujol) 3520(w), 3480(m), 3200(w), 3150(w), 3000(m), 1625(s),

1600(s), 1350(s), 1310(m), 1125(m), 1100(m), 1065(m), 1050(m), 1010(m), 975(m), 760(m) cm$^{-1}$.

$^1$HNMR: (in D$_2$O, ppm from TMS as external standard TMS, δ) 2.69(s satellite J$_{195Pt-H}$=30 Hz, CH$_3$), 2.90(s, satellite J$_{195Pt-H}$=24 Hz, CH$_3$), 4.75(s, satellite J$_{195Pt-H}$=21 Hz —CH$_2$—).

EXAMPLE 9

(trans-Dichloro)(glycolato-O,O')bis(methylamine)-platinum (IV) 14

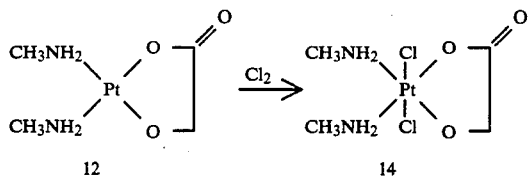

To an aqueous solution (2.5 ml) of 2.32 g (7.00 mmol) of (glycolato-O,O')bis(methylamine)platinum(II) 12 was added 146 ml of 0.048M aqueous chlorine. The mixture was allowed to stand at room temperature for 1.5 hours, neutralized with 1N NaOH to pH 7.0, and dried up at a temperature lower than 30° C. The resulting residue was passed through a column of silica-gel and eluted with methanol-acetone (1:4 v/v). The eluate of which the Rf value was 0.66 on a thin layer chromatography (hereinafter abbreviated as "tlc") was collected, evaporated, and recrystallized from methanol to give 0.62 g (yield: 22%) of yellow crystalline compound 14 in the form of methanol adduct.

m.p.: 176°-178° C.

Anal. Calcd. (%) [for C$_4$H$_{12}$N$_2$O$_3$C$_2$Pt(CH$_3$OH)$_{0.13}$]: C, 12.20; H, 3.11; N, 6.89; Cl, 17.45; Pt, 48.01. Found (%): C, 12.01; H, 3.19; N, 6.90; Cl, 17.83; Pt, 47.22.

IR: ν$_{max}$(Nujol) 3220(m), 3170(m), 3060(m), 1630(s), 1575(m), 1420(w), 1410(m), 1340(m), 1310(m), 1285(sh), 1115(m), 1100(m), 1040(m), 1000(w), 920(m), 800(w), 755(m), 715(w) cm$^{-1}$.

EXAMPLE 10

(trans-Diiodo)(glycolato-O,O')bis(methylamine)-platinum(IV) 15

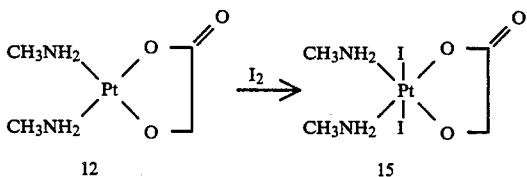

A solution of 0.254 g (1.00 mmol) of iodine in 5 ml of ethanol was added to an aqueous solution (12 ml) of 0.331 g (1.00 mmol) of (glycolato-O,O')bis(methylamine)platinum(II) 12. The mixture was stirred at room temperature for 2 hours and the resulting black-purple material was collected by filtration and crystallized from water to give 0.447 g of the titled compound 15 as monohydrate.

Yield: 74%.

m.p.: 135°-137° C. (decomp.).

Anal. Calcd. (%) [for C$_4$H$_{12}$O$_3$N$_2$I$_2$Pt(H$_2$O)$_{1.0}$]: C, 7.97; H, 2.34; N, 4.65; I, 42.09; Pt, 32.35. Found (%): C, 7.75; H, 2.57; N, 4.65; I, 41.77; Pt, 31.90.

IR: ν$_{max}$(Nujol) 3490(m), 3150(br, m), 1650(s), 1610(sh), 1570(m), 1447(s), 1407(m), 1340(s), 1300(s), 1290(sh), 1220(w), 1100(s), 1095(sh), 1055(s), 995(m), 920(m), 765(m) cm$^{-1}$.

$^1$HNMR: (in D$_2$O, ppm from TMS as external standard TMS, δ) 2.42(s satellite J$_{195Pt-H}$=25 Hz, CH$_3$), 4.01(s, satellite J$_{195Pt-H}$=21 Hz).

EXAMPLE 11

(trans-Dihydroxo)(glycolato-O,O')(ethane-1,2-diamine)-platinum(IV) 17

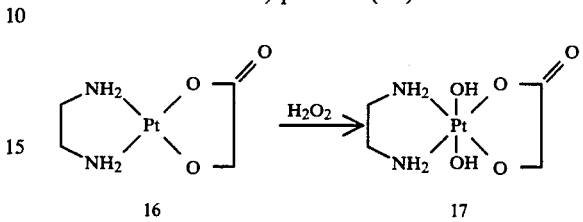

(Glycolato-O,O')(ethane-1,2-diamine)platinum(II) 16 (1.68 g, 2.04 mmol) was dissolved in 32 ml of water with heating at 65° C. to which was added 0.49 ml (4.32 mmol) of 30% aqueous hydrogen peroxide at room temperature. The mixture was stirred for 3.5 hours and concentrated to about 1 ml under reduced pressure at 45° C. The resulting colorless crystals were collected by filtration and dried under reduced pressure at room temperature to give 0.54 g (yield: 64.7%) of the titled compound 17 as dihydrate.

m.p.: 185° C.~(decomp.)

Anal. Calcd. (%) [for C$_4$H$_{12}$N$_2$O$_5$Pt(H$_2$O)$_{2.0}$]: C, 11.85; H, 3.96; N, 6.86; Pt, 48.48; H$_2$O, 8.61. Found (%): C, 12.03; H, 4.04; N, 7.02; Pt, 48.86; H$_2$O, 9.02.

IR: ν$_{max}$(Nujol) 3440(s), 3210(sh), 1660(s), 1603(s), 1450(m), 1422(w), 1340(s), 1300(s), 1202(w), 1064(m), 1047(m), 912(m), 885(w) cm$^{-1}$.

$^1$HNMR: (in D$_2$O, ppm from TMS as external standard, δ) 3.35(s, satellite J$_{195Pt-H}$=27 Hz, N—CH$_2$—CH$_2$—N), 4.75(s, satellite J$_{195Pt-H}$=21 Hz, —O-C—CH$_2$—O—).

EXAMPLE 12

(trans-Dihydroxo)(glycolato-O,O')(ethane-1,2-diamine)-platinum(IV) disodium salt 18

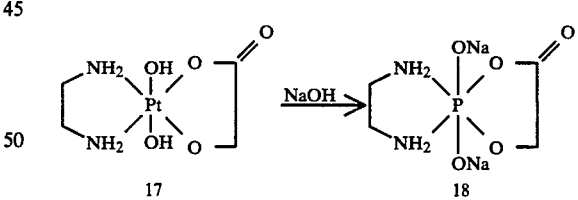

A mixture of 0.25 g (0.63 mmol) of (trans-dihydroxo)(glycolato-O,O')(ethane-1,2-diamine)platinum(IV) 17 (described in Example 11) and 12.6 ml (1.26 mmol) of 0.1N NaOH was stirred at room temperature for 1 hour and heated up to 60° C., whereby the solid in the mixture was dissolved. The resulting solution was concentrated at 55° C. and dried under reduced pressure at 50° C. to give 0.3 g (yield: 99.3%) of pale brownish hygroscopic titled compound 18 as 4 mol hydrate.

Anal. Calcd. (%) [for C$_4$H$_{10}$N$_2$O$_5$Na$_2$Pt(H$_2$O)$_{4.0}$]: C, 10.02; H, 3.79; N, 5.85; Na, 9.59; Pt, 40.71; H$_2$O, 15.04. Found (%): C, 10.18; H, 3.72; N, 6.15; Na, 9.39; Pt, 41.70; H$_2$O, 14.31.

$^1$HNMR: (in D$_2$O, ppm from TMS as external standard, δ) 3.42(s, satellite J$_{195Pt-H}$=27 Hz, N—CH$_2$CH- 2—N), 4.18(s, satellite $J_{195Pt-H}=27$ Hz, CO—CH$_2$—O).

EXAMPLE 13

(trans-Dibromo)(glycolato-O,O')(ethane-1,2-diamine)-platinum(IV) 19

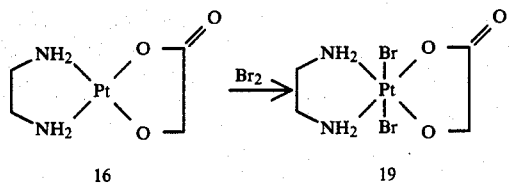

(Glycolato-O,O')(ethane-1,2-diamine)platinum(II) 16 (1.5 g, 4.56 mmol) was dissolved in 50 ml of water with heating and 0.36 g (4.51 mmol) of bromine was added thereto at room temperature with stirring. The suspension containing yellowish orange material was stirred for 2 hours and the resulting solid was collected by filtration and dried at 50° C. under reduced pressure.

The yield of 19: 0.5 g (22.3%).

Anal. Calcd. (%) [for $C_4H_{10}N_2O_3Br_2Pt$]: C, 9.82; H, 2.06; N, 5.73; Br, 32.68; Pt, 39.89. Found (%): C, 9.58; H, 2.12; N, 5.81; Br, 31.56; Pt, 40.51.

IR: $\nu_{max}$(Nujol) 3213(w), 3160(w), 3078(m), 1661(vs), 1583(m), 1569(w), 1337(m), 1268(s), 1277(sh), 1190(w), 1132(m), 1060(m), 1048(m), 1021(w), 991(w), 912(m) cm$^{-1}$.

EXAMPLE 14

(trans-Dihydroxo)(lactato-O,O')(ethane-1,2-diamine)-platinum(IV) 23

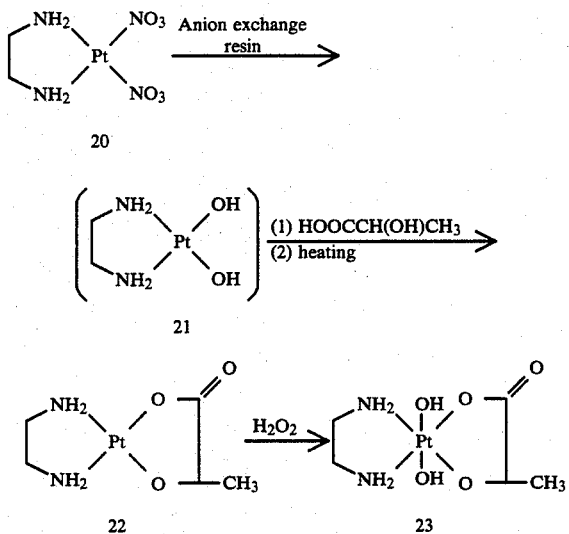

14-(1):

Preparation of (lactato-O,O')(ethane-1,2-diamine)-platinum(II) 22

An aqueous solution of 0.15 g (0.39 mmol) of (cis-dinitrato)(ethane-1,2-diamine)platinum(II) 20 (known compound) was passed through a column of Diaion SA-10 (OH type). To alkaline eluate (i.e., an aqueous solution of the compound 21) was added 0.036 g (0.39 mmol) of lactic acid. The mixture was allowed to stand for 6 hours, concentrated to 0.2 ml, and dried over silica-gel in a desiccator for 6 days. The resulting needles were washed with a small amount of ethanol and dried under reduced pressure.

Yield of the compound 22: 0.024 g (18%).

m.p.: 205° C. ~(decomp.)

Anal. Calcd. (%) [for $C_5H_{12}N_2O_3Pt$]: C, 17.50; H, 3.52; N, 8.16; Pt, 56.84. Found (%): C, 16.16; H, 3.52; N, 8.21; Pt, 56.66.

IR: $\nu_{max}$(Nujol) 3250(sh), 3170(m), 1670(s), 1625(s), 1365(sh), 1285(m), 1110(m), 1050(m), 870(m), 780(w), 725(w) cm$^{-1}$.

$^1$HNMR: (in D$_2$O, ppm from TMS as external standard, δ) 1.72(d, CH$_3$), 2.95(s, satellite $J_{195Pt-H}=44$ Hz, N—CH$_2$CH$_2$—N), 4.57

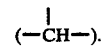

14-(2):

Preparation of the compound 23

To an aqueous solution (3.5 ml) of 0.21 g (0.596 mmol) of the compound 22 was added 0.6 ml (1.76 mmol) of 10% hydrogen peroxide. The mixture was stirred for 1 hour and concentrated at 40° C. under reduced pressure. The precipitating crystals were collected by filtration and recrystallized from water to give 0.094 g of the titled compound 23

Yield: 42%.

m.p.: 182° C. ~(decomp.).

Anal. Calcd. (%) [for $C_5H_{14}O_5N_2Pt$]: C, 15.92; H, 3.74; N, 7.43; Pt, 51.71. Found (%): C, 15.63; H, 4.05; N, 7.54; Pt, 51.73.

IR$_{max}$: $\nu_{max}$(Nujol) 3450(sh), 3100(sh), 1670(br, s), 1590(m), 1360(w), 1335(w), 1250(s), 1100(m), 1050(sh), 1040(s), 1000(sh), 910(w), 860(s), 770(m), 715(w), 650(w) cm$^{-1}$.

$^1$HNMR: (in D$_2$O, ppm from TMS as external standard, δ) 1.81(d, J=7 Hz, CH$_3$), 2.99–3.50(br-.N—CH$_2$CH$_2$—N), 4.93($J_{195Pt-H}=21$ Hz, —CH—).

EXAMPLE 15

(trans-Dihydroxo)(β-chlorolactato-O,O')(ethane-1,2-diamine)platinum(IV) 25

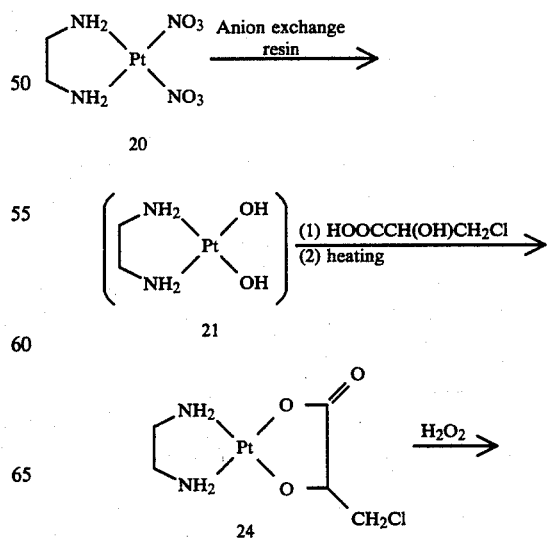

-continued

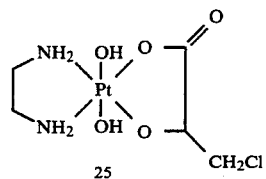

15-(1):

Preparation of (β-chlorolactato-O,O')(ethane-1,2-diamine)platinum(II) 24

(Dinitrato)(ethane-1,2-diamine)platinum(II) 20 (known compound) (3.5 g, 9.23 mmol) was dissolved in 60 ml of water with heating. The mixture was cooled and passed through 100 ml of a column of an anion exchange resin Diaion SA-10A (OH type). To 120 ml of alkaline eluant (i.e., an aqueous solution of the compound 21) was added an aqueous solution of 1.15 g (9.24 mmol) of β-chlorolactic acid dissolved in 15 ml of water. The mixture was concentrated to about 110 ml at 40°–50° C. (pH=6.8). The resulting mixture was stirred at 53°–58° C. for about 22 hours and insoluble material was removed by filtration. The solution was concentrated and the residue was purified by silica-gel chromatography [developer: $H_2O(2)$-ethanol(5)] and recrystallized from water to give 1.12 g (yield: 30.3%) of the titled compound 24 as hydrate.

m.p.: 180° C. ~(decomp.).

Anal. Calcd. (%) [for $C_5H_{11}N_2O_3ClPt(H_2O)_{1.2}$]: C, 15.04; H, 3.38; N, 7.02; Cl, 8.88; Pt, 48.85; $H_2O$, 5.41. Found (%): C, 15.10; H, 3.40; N, 7.03; Cl, 8.82; Pt, 48.86; $H_2O$, 5.42.

IR: $\nu_{max}$(Nujol) 3330(m), 3278(m), 3200(m), 3081(s), 1637(s, br), 1403(m), 1360(s), 1303(m), 1279(m), 1250(w), 1212(w), 1173(w), 1160(w), 1089(s), 1056(s), 918(m), 887(w), 883(m) cm$^{-1}$.

$^1$HNMR: (in $D_2O$, ppm from TMS as external standard, δ) 2.98(s, satellite $J_{195Pt-H}$=45 Hz, N—CH$_2$CH$_2$—N), 4.15(d, CH$_2$—Cl), 4.82(t, —CH—).

15-(2):

Preparation of the compound 25

The compound 24 (0.948 g, 2.37 mmol) was dissolved in 48 ml of water with heating and the solution was cooled. To the mixture was added 0.57 ml (0.171 g, 5.03 mmol) of 30% hydrogen peroxide, which was stirred at room temperature for 5 hours. The resulting mixture was concentrated to 2 ml at 45°–55° C. under reduced pressure and the pale yellow crystals were collected by filtration and dried at room temperature under reduced pressure for 1 hour to give 0.72 g (yield: 73.8%) of the titled compound 25 as hydrate.

m.p.: 185° C. ~(decomp.).

Anal. Calcd. (%) [for $C_5H_{13}N_2O_5ClPt(H_2O)_{0.3}$]: C, 14.40; H, 3.29; N, 6.72; Cl, 8.50; Pt, 46.76. Found (%): C, 13.96; H, 3.08; N, 6.81; Cl, 8.34; Pt, 46.76.

IR: $\nu_{max}$(Nujol) 3545(sh), 3500(m), 3426(s), 3275(m), 1671(s), 1645(sh), 1587(m), 1431(w), 1357(s), 1319(s), 1295(s), 1086(m), 1053(m), 942(w), 910(w), 896(w), 855(w), 830(w), 732(m) cm$^{-1}$.

EXAMPLE 16

(trans-Dihydroxo)(mandelato-O,O')(ethane-1,2-diamine)platinum(IV) 27

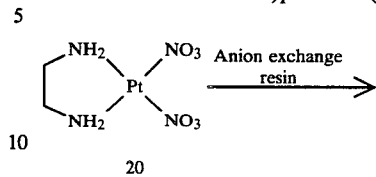

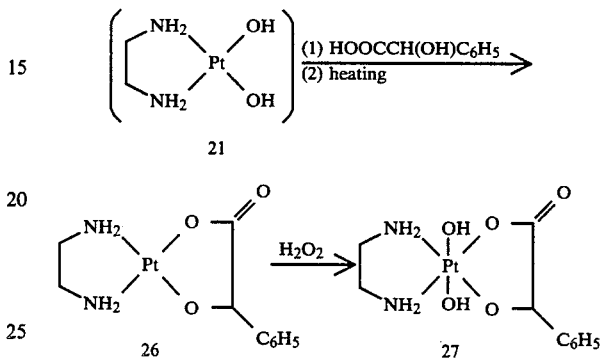

16-(1):

Preparation of (mandelato-O,O')(ehtane-1,2-diamine)-platinum(II) 26

(Dinitrato)(ethane-1,2-diamine)platinum(II) 20 (known compound) (1.96 g, 5.17 mmol) was dissolved in 30 ml of water; and the mixture was cooled and passed through a column of 70 ml of an anion exchange resin Diaion SA-10A (OH type). To about 100 ml of alkaline eluate (i.e., an aqueous solution of the compound 21) was added a solution of 0.787 g (5.18 mmol) of DL-mandelic acid in 17.5 ml of water. The mixture was stirred at 53°–58° C. for 15 hours and the resulting red-brownish suspension was concentrated to about 3 ml at 45°–55° C. under reduced pressure. The residue was collected by filtration and recrystallized from water to give 1.41 g (yield: 67.3%) of the titled compound 26.

m.p.: 240° C. ~(decomp.).

Anal. Calcd. (%) [for $C_{10}H_{14}N_2O_3Pt$]: C, 29.63; H, 3.48; N, 6.91; Pt, 48.13. Found (%): C, 29.32; H, 3.50; N, 6.93; Pt, 48.13.

IR: $\nu_{max}$(Nujol) 3280(s), 3240(w), 3160(s), 1657(vs), 1621(s), 1580(s), 1489(w), 1450(s), 1315(s), 1255(w), 1172(m), 1135(w), 1058(m), 1040(s), 943(m), 807(s), 710(m), 697(s) cm$^{-1}$.

16-(2): Preparation of the compound 27

The compound 26 (1.04 g, 2.57 mmol) was dissolved in 300 ml of water with heating, and 0.62 ml (0.186 g, 5.47 mmol) of 30% hydrogen peroxide was added thereto. The mixture was stirred at room temperature for 5 hours and concentrated to 5 ml at 45°–50° C. The precipitating crystalline material was collected by filtration, washed with a small amount of water, and dried under reduced pressure to give 1.03 g (yield: 88.7%) of yellowish compound 27.

m.p.: 260° C. ~(decomp.).

Anal. Calcd. (%) [for $C_{10}H_{16}N_2O_5Pt(H_2O)_{0.65}$]: C, 26.63; H, 3.87; N, 6.21; Pt, 43.25; $H_2O$, 2.60. Found (%): C, 26.04; H, 3.87; N, 6.29; Pt, 43.87; $H_2O$, 2.58.

IR: $\nu_{max}$(Nujol) 3518(m), 3176(s), 3103(s), 1687(vs), 1592(m), 1450(sh), 1301(w), 1274(s), 1242(m), 1050(m), 1038(sh), 1018(m), 1000(w), 942(w), 813(w), 698(m) cm$^{-1}$.

EXAMPLE 17

(trans-Dihydroxo)(glycolato-O,O')(cis-cyclohexane-1,2-diamine)platinum(IV) 31

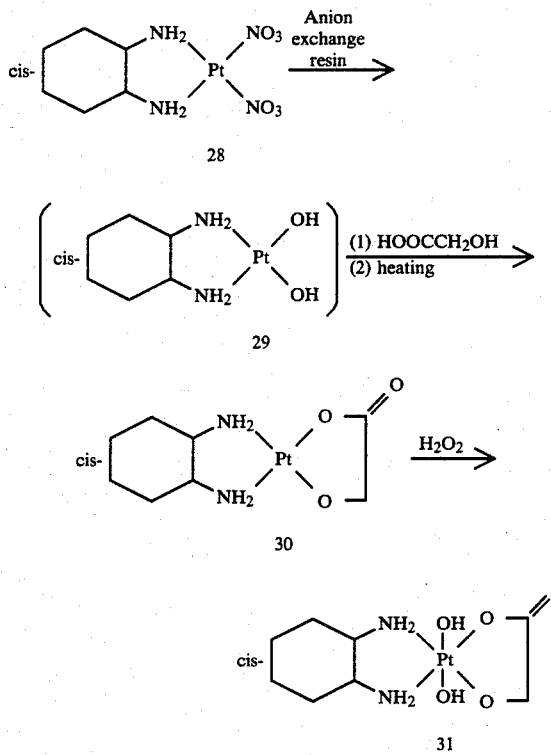

17-(1): Preparation of (glycolato-O,O')(cis-cyclohexane-1,2-diamine)-platinum(II) 30

(Dinitrato)(cis-cyclohexane-1,2-diamine)platinum(II) 28 (known compound) (2.95 g, 6.81 mmol) was dissolved in 50 ml of water with heating. The mixture was cooled and passed through a column of 180 ml of an anion exchange resin Diaion SA-10A (OH type).

A mixture of 150 ml of alkaline eluate (i.e., an aqueous solution of the compound 29) and 0.533 g (7.01 mmol) of glycolic acid was stirred for 10 minutes and concentrated to 8 ml at 40°–50° C. under reduced pressure. The resulting mixture was dried over silica-gel in a desiccator for 4 days. The residue was purified by silica-gel column chromatography [developer: H$_2$O-ethanol(1:5 v/v)(5)] and recrystallized from water-ethanol to give 0.836 g (yield: 32%) of the compound 30.

m.p.: 217° C. ~(decomp.).

Anal. Calcd. (%) [for C$_8$H$_{16}$N$_2$O$_3$Pt(H$_2$O)$_{0.5}$]: C, 24.49; H, 4.36; N, 7.14; Pt, 49.72. Found (%): C, 24.48; H, 4.28; N, 7.43; Pt, 50.59.

IR: $\nu_{max}$(Nujol) 3170(m), 3055(m), 1605(s), 1435(w), 1335(w), 1318(w), 1285(w), 1260(w), 1245(w), 1230(m), 1167(w), 1135(m), 1100(w), 1080(w), 1060(m), 1035(w), 980(w), 935(w), 880(w), 845(w), 830(w), 770(w) cm$^{-1}$.

$^1$HNMR: (in D$_2$O, ppm from TMS as external standard, δ) 1.73–2.53, 2.93–3.90(b, cyclohexyl), 4.50(s, satellite J$_{195Pt-H}$=33 Hz, —CH$_2$—).

17-(2): Preparation of the compound 31

The compound 30 (1.06 g, 2.72 mmol) was dissolved in 10 ml of water with heating. The mixture was cooled, and mixed with 2.3 ml (6.7 mmol) of 10% aqueous hydrogen peroxide. The resulting mixture was stirred at room temperature for 1 hour and concentrated at about 40° C. under reduced pressure. The precipitating white crystalline material was collected by filtration and concentrated at room temperature under reduced pressure to give 0.768 g (ield: 66.7%) of the titled compound 31 as 0.5 mol hydrate.

m.p.: 160° C. ~(decomp.).

Anal. Calcd. (%) [for C$_8$H$_{18}$N$_2$O$_5$Pt(H$_2$O)$_{0.5}$]: C, 22.54; H, 4.99; N, 6.57; Pt, 45.76. Found (%): C, 22.57; H, 4.53; N, 6.80; Pt, 45.78.

IR: $\nu_{max}$(Nujol) 3500(s), 3200(m), 3130(s), 1700(sh), 1600(s), 1605(sh), 1595(s), 1420(w), 1390(w), 1335(s), 1300(s), 1230(w), 1170(w), 1090(w), 1060(m), 1030(w), 985(m), 940(w), 910(m), 890(w), 870(w), 850(w), 805(w), 760(m), 715(m), 645(m) cm$^{-1}$.

$^1$HNMR: (in D$_2$O, ppm from TMS as external standard, δ) 1.70–2.50(b, cyclohexyl), 3.46–4.33 (b, cyclohexyl CH—N), 4.70(s, satellite J$_{195-Pt-H}$=21 Hz).

EXAMPLE 18

(trans-Dihydroxo)(glycolato-O,O')(trans-l-cyclohexane-1,2-diamine)platinum(IV) 33

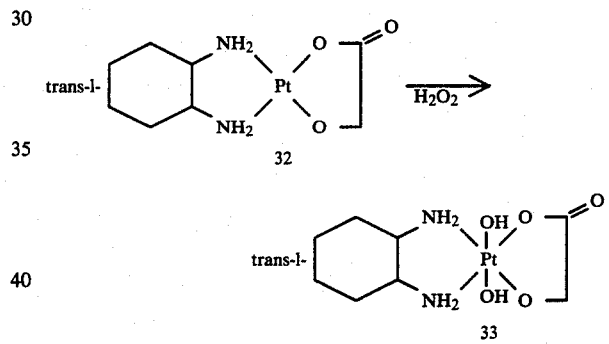

To a solution of 0.862 g (2.20 mmol) of (glycolato-O,O')(trans-l-cyclohexane-1,2-diamine)platinum(II) 32 0.5 hydrate in 40 ml of water was added 2.25 ml (6.6 mmol) of 10% aqueous hydrogen peroxide. The mixture was stirred for 10 minutes. The precipitating white crystalline material was collected by filtration and recrystallized from water to give 0.781 g of the compound 33 as 0.5 mol hydrate.

Yield: 83%.

m.p.: 190° C. ~(decomp.).

Anal. Calcd. (%) [for C$_8$H$_{18}$N$_2$O$_5$Pt(H$_2$O)$_{0.5}$]: C, 22.54; H, 4.49; N, 6.57; Pt, 45.76. Found (%): C, 22.37; H, 4.16; N, 6.71; Pt, 45.71.

IR: $\nu_{max}$(Nujol) 3380(s), 3150(br, s), 1690(s), 1615(m), 1590(s), 1350(w), 1315(s), 1295(w), 1280(s), 1200(w), 1140(w), 1090(w), 1070(w), 1045(s), 915(w), 900(m), 840(w), 815(w), 760(w), 655(w) cm$^{-1}$.

$^1$HNMR: (in D$_2$O, ppm from TMS as external standard, δ) 1.50–2.33, 2.56–2.85(br, cyclohexyl), 3.06–3.33(br, N—CH), 4.70(s, satellite J$_{195-Pt}$=21 Hz, glycolato CH$_2$—).

EXAMPLE 19

(trans-Dihydroxo)(glycolato-O,O')[cyclohexane-1,1-bis(methylamine)]platinum(IV) 37

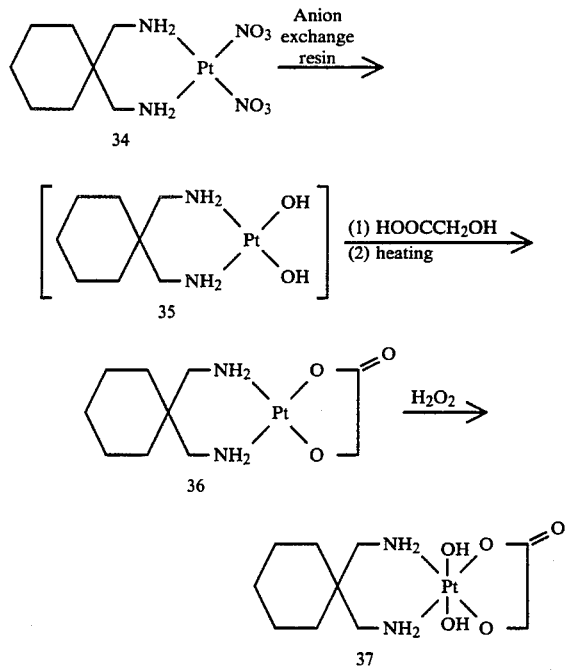

19-(1): Preparation of (glycolato-O,O')[cyclohexane-1,1-bis(methylamine)]-platinum(II) 36

(Dinitrato)[cyclohexane-1,1-bis(methylamine)]-platinum(II) 34 was passed through a column of an anion exchange resin Diaion SA-10A (OH type). To an alkaline eluate (i.e., an aqueous solution of the compound 35, 2.0 mmol) was added 0.148 g (1.95 mmol) of glycolic acid. The mixture was heated at 55° C. for 6 hours. The reaction mixture was concentrated. The residual solid was dissolved in metahnol and purified by silica-gel column chromatography. This was recrystallized from methanol-acetone to give 0.30 g of the titled compound 36 as colorless crystals.

Yield: 37%.

m.p.: 205°–210° C.

Anal. Calcd. (%) [for $C_{10}H_{20}N_2O_3Pt$]: C, 29.20; H, 4.90; N, 6.81; Pt, 47.42 Found (%): C, 28.70; H, 4.79; N, 6.81; Pt, 47.10.

IR: $\nu_{max}$(Nujol) 3360(w), 3200(m), 3130(m), 1650(s), 1340(m), 1300(m), 1240(w), 1170(w), 1150(w), 1050(m), 1010(w), 910(w), 720(w) cm$^{-1}$.

$^1$HNMR: (in $D_2O$, ppm from TMS as external standard, δ) 1.88(br, cyclohexyl), 2.95(s, satellite $J_{195Pt-H}=50$ Hz, $CH_2$—N), 2.97(s, satellite $J_{195Pt-H}=43$ Hz, $CH_2$—n), 4.85(s, satellite $J_{195Pt-H}=34$ Hz, glycolato —$CH_2$—).

19-(2): Preparation of the compound 37

To a solution of 0.10 g (0.243 mmol) of the compound 36 in 5 ml of water was added 0.06 g (0.54 mmol) of 30% aqueous hydrogen peroxide. The mixture was stirred at room temperature for 3 hours and concentrated at 35° C. under reduced pressure. The residue was concentrated at room temperature under reduced pressure to give 0.11 g of the titled compound 37 m.p.: 170° C.~(decomp.).

Anal. Calcd. (%) [for $C_{10}H_{22}N_2O_5Pt(H_2O)_{2.0}$]: C, 24.95; H, 5.44; N, 5.82; Pt, 40.52. Found (%): C, 24.85; H, 4.95; N, 5.38; Pt, 40.41.

IR: $\nu_{max}$(Nujol 3550–3250(br, m), 3250–3000(br, m), 1665(s), 1595(s), 1340(m), 1290(s), 1168(w), 1032(m), 910(m), 780(w) cm$^{-1}$.

$^1$HNMR: (in $D_2O$, ppm from TMS as external standard, δ) 1.97(br, cyclohexyl), 2.97(N—$CH_2$), 2.88(s, satellite $J_{195Pt-H}=21$ Hz glycolato —$CH_2$—).

EXAMPLE 20 af-Dihydroxo-bc-(glycolato-O,O')-de-[trans-(1-aminomethyl)-2-aminocyclohexane]platinum(IV) and af-dihydroxo-cb-(glycolato-O,O')-de-[trans-(1-aminomethyl)-2-aminocyclohexane]platinum(IV) 42A, 42B

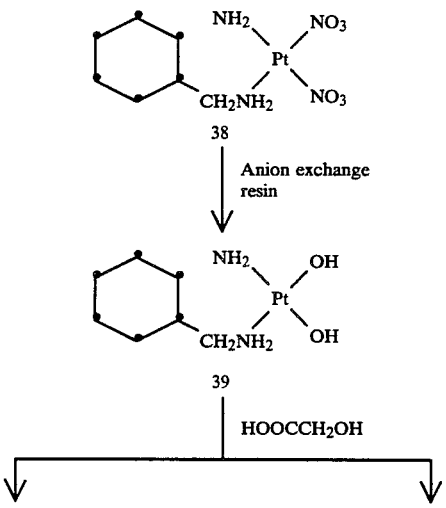

-continued

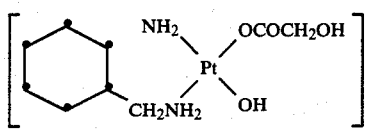

40A

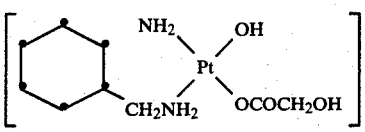

40B

↓ Heating

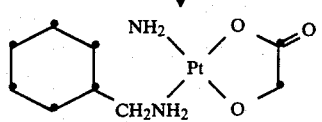

41A

↓ H₂O₂

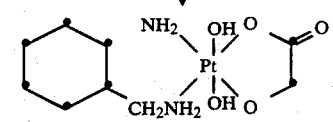

42A

↓ Heating

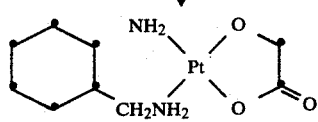

41B

↓ H₂O₂

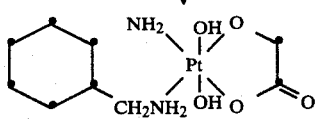

42B 20-(1): Preparations of
ab-(glycolato-O,O')-cd-[trans-(1-aminomethyl)-2-aminocyclohexane]platinum(II) and
ba-(glycolato-O,O')-cd-[trans-(1-aminomethyl)-2-aminocyclohexane]platinum(II) 41A, 41B (Dinitrato)[trans-(1-aminomethyl-2-aminocyclohexane]platinum(II) 38 (0.650 g, 1.45 mmol) was dissolved in 6.5 ml of water with heating. The mixture was cooled and passed through a column of Diaion SA-10A (OH type) to give an aqueous solution of the compound 39. To the aqueous solution was added 0.110 g (1.45 mmol) of glycolic acid to give a mixture of the intermediary compounds 40A and 40B.

The mixture was heated at 60° C. for 6 hours to give chelate compounds 41A and 41B. The reaction mixture was concentrated under reduced pressure and the resulting solid was washed with a small amount of ethanol to give 0.50 g of crude products. The crude products contained two geometrical isomers 41A and 41B, and showed 2 spots on tlc. The Rf values of the compounds 41A and 41B were 0.39 and 0.29 (developer: 95% methanol). The compounds 41A and 41B were separated from each other by silica-gel column chromatography and successive recrystallization from water-methanol. It has not yet been elucidated which isomer of the isolated two isomers correspond to the compounds of the structural formula 41A or 41B.

Anal. Calcd. (%) [for C₉H₂₀N₂O₄Pt]: C, 26.03; H, 4.85; N, 6.74. Found (%): 41A.H₂O or 41B.H₂O C, 26.25; H, 4.62; N, 6.63, 41B.H₂O or 41A.H₂O C, 25.73; H, 4.64; N, 6.86.

m.p.: 41A.H₂O or 41B.H₂O 205° C.~(decomp.) 41B.H₂O or 41A.H₂O 200°-210° C. (decomp.).

IR: $\nu_{max}$(Nujol): 41A.H₂O or 41B.H₂O: 3350(m), 3150(s), 3080(s), 1635(s), 1360(m), 1350(s), 1310(m), 1265(w), 1205(w), 1060(m), 960(w), 915(m), 880(w), 740(m), 720(w) cm⁻¹. 41B.H₂O or 41A.H₂O: 3350(m), 3150(s), 3050(m), 1620(s), 1360(m), 1340(s), 1300(m), 1180(w), 1060(m), 995(w), 960(w), 915(m), 880(w), 760(m), 720(w) cm⁻¹.

¹HNMR: (in D₂O, ppm from TMS as external standard, δ) 41A.H₂O or 41B.H₂O: 1.2-3.4(bm, cyclohexyl and substituent CH, CH₂), 4.57(s, satellite $J_{195Pt-H}=33$ Hz, glycolato CH₂). 41B.H₂O or 41A.H₂O: 1.2-3.4(bm, cyclohexyl and substituent CH, CH₂), 4.57(s, satellite $J_{195Pt-H}=33$ Hz, glycolato CH₂).

20-(2): Preparations of the compounds 42A and 42B

To an aqueous solution of 0.40 g (1.00 mmol) of one of the isomers 41A.H₂O and 41B.H₂O in 2 ml of water was added 0.075 g of 10% hydrogen peroxide. The mixture was allowed to stand at room temperature for 1 hour and concentrated at lower than 30° C. under reduced pressure. The residue was recrystallized from water-metahnol to give 0.038 g of the compound 42A.H₂O or 42B.H₂O as colorless crystals.

The other isomer (41B.H₂O or 41A.H₂O) (0.40 g, 1.00 mmol) was cooled in 2 ml of water and 0.075 g of 10% aqueous hydrogen peroxide was added thereto. Then, the reaction was carried out in the same manner as described above to give 0.035 g of the compound 42B.H₂O or 42A.H₂O as colorless crystals.

Anal. Calcd. (%) [for C₉H₂₂N₂O₆Pt]: C, 24.05; H, 4.94; N, 6.23. Found (%): 42A.H₂O or 42B.H₂O C, 24.50; H, 4.58; N, 6.47, 42B.H₂O or 42A.H₂O C, 23.61; H, 4.76; N, 6.27.

m.p.: 42A.H₂O or 42B.H₂O 215° C.~(decomp.) 42B.H₂O or 42A.H₂O 205° C.~(decomp.).

IR: $\nu_{max}$(Nujol) 42A.H₂O or 42B.H₂O: 3450(sh), 3420(m), 3120(m), 1700(s), 1630(m), 1340(m), 1300(w), 1265(m), 1100(m), 1020(m), 970(w), 900(m), 770(m), 720(w) cm⁻¹. 42B.H₂O or 42A.H₂O: 3460(s), 3330(m), 3150(sh), 3080(s), 1670(s), 1610(m), 1420(m), 1335(m), 1280(m), 1085(m), 1040(m), 1000(w), 960(w), 910(m), 760(m), 720(w) cm⁻¹.

¹HNMR: (in D₂O, ppm from TMS as external standard, δ): 42A H₂O or 42B H₂O: 1.3-1.4(bm, cyclohexyl and substituent CH, CH₂), 4.73(s, satellite $J_{195Pt-H}=21$ Hz, glycolato CH₂). 42B H₂O or 42A H₂O: 1.3-1.4(bm, cyclohexyl and substituent CH, CH₂), 4.73(s, satellite $J_{195Pt-H}=21$ Hz, glycolato CH₂).

EXAMPLE 21

(trans-Dihydroxo)(glycolato-O,O')(exo-cis-bicyclo[2.2.1]heptane-2,3-diamine)platinum(IV) 44

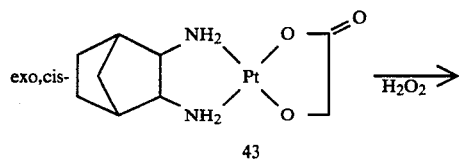

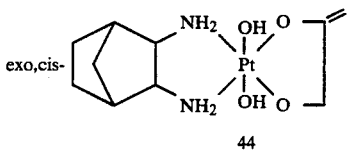

To a solution of 0.040 g (1.00 mmol) of (glycolato-O,O')(exo,cis-bicyclo[2.2.1]heptane-2.3-diamine)-platinum(II) 43 in 4 ml of water was added 0.075 g of 10% aqueous hydrogen peroxide. The mixture was allowed to stand at room temperature for 1 hour and cooled. The precipitating crystals were collected by filtration, washed with a small amount of water, and dried at room temperature for a while to give 0.030 g of the compound 44 as trihydrate.

Anal. Calcd. (%) [for $C_9H_{22}N_2O_5Pt$]: C, 24.05; H, 4.93; N, 6.23. Found (%): C, 24.20; H, 4.84; N, 6.30.

m.p.: gradually decomposed at higher than 220° C.

IR: $\nu_{max}$: (Nujol) 3500(sh), 3400(m), 3180(sh), 3120(s), 1700(m), 1675(m), 1645(sh), 1605(m), 1340(w), 1300(m), 1280(sh), 1150(w), 1040(sh), 1030(m), 995(w), 915(m), 765(m), 720(w) cm$^{-1}$.

EXAMPLE 22

(trans-Dihydroxo)(glycerato-O,O')(exo,cis-bicyclo[2.2.1]heptane-2,3-diamine)platinum(IV) 48

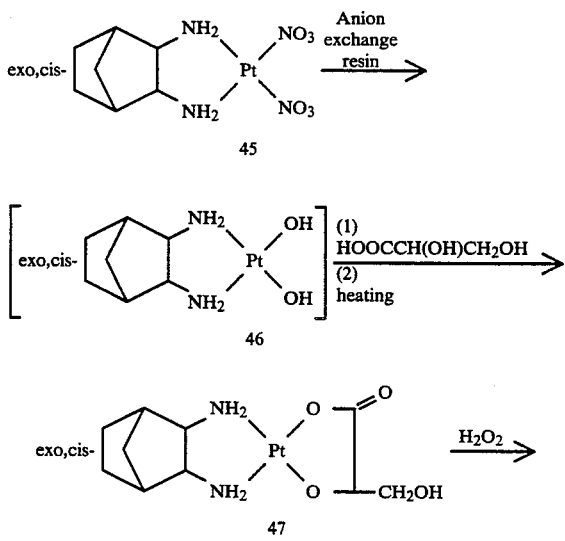

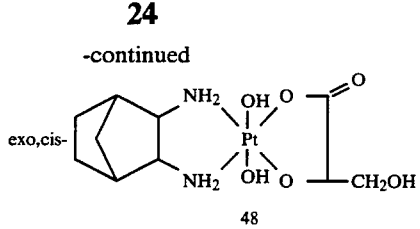

22-(1): Preparation of (glycerato-O,O')(exo,cis-bicyclo[2.1.1]heptane-2,3-diamine)platinum(II) 47

(Dinitrato)(exo,cis-bicyclo[2.2.1]heptane-2,3-diamine)platinum(II) 45 was passed through an anion exchange resin Diaion SA-10A to give the dihydroxo-compound 46.

To 2.5 mmol (150 ml) of an aqueous solution of the dihydroxo-compound 46 was added 60 ml of an aqueous solution of 2.4 mmol of DL-glyceric acid. The mixture was allowed to react at room temperature for 3 days and at an elevated temperature of 55° C. for 6 hours.

The reaction mixture was concentrated and dissolved in methanol at a ratio of 10%.

The methanol solution was purified by silica-gel column chromatography and recrystallized from methanol-acetone to give 0.45 g of the compound 47 as colorless crystals.

Yield: 42%.

m.p.: 200° C. ~(decomp.).

Anal. Calcd. (%) [for $C_{10}H_{18}N_2O_4Pt$]: C, 28.23; H, 4.27; N, 6.59; Pt, 45.86. Found (%): C, 27.75; H, 4.48; N, 6.78; Pt, 44.23.

IR: $\nu_{max}$(Nujol) 3380(m), 3200(s), 3100(s), 1625(s), 1350(m), 1140(w), 1100(m), 1050(m), 1040(m), 1010(w), 950(w), 880(w), 800(w) cm$^{-1}$.

$^1$HNMR: (in $D_2O$, ppm from TMS as external standard, δ) 1.4–2.1(m, bicyclo[2.2.1]heptane $C_{5,6}$), 1.66(bd, J=12 bicyclo[2.2.1]heptane $C_7$ anti H), 2.65(bs, bicyclo[2.2.1]heptane $C_{1,4}H$), 2.82(bd, J=12 bicyclo[2.2.1]heptane $C_7$Sym H), 3.44(d, J=1.5, $^{195}$Pt—H satellite J=27, norbornyl $C_{2,3}H$), 4.19(d, J=4.2 glyceryl $CH_2$), 4.51(t, J=4.2, $^{195}$Pt satellite J=33, glyceryl CH).

22-(2): Preparation of the compound 48

To a solution of 0.148 g (0.348 mmol) of the compound 47 in 10 ml of water was added 0.3 ml (0.882 mmol) of 10% hydrogen peroxide at room temperature. The mixture was stirred for 1 hour and concentrated at 40° C. under reduced pressure.

The precipitating crystals were collected by filtration, washed with a samll amount of water, and dried under reduced pressure to give 0.133 g of the compound 48 as 0.5 mole hydrate.

Yield: 69.6%.

m.p.: 187° C. ~(decomp.).

Anal. Calcd. (%) [$C_{10}H_{20}N_2O_5Pt(H_2O)_{0.5}$]: C, 25.64; H, 4.52; N, 5.98; Pt, 41.65. Found (%): C, 25.52; H, 4.39; N, 6.16; Pt, 41.81.

IR: $\nu_{max}$(Nujol) 3460(s), 3425(s), 3210(s), 3160(s), 3075(s), 1680(vs), 1600(s), 1580(s), 1350(sh), 1330(s), 1310(m), 1300(m), 1280(m), 1260(m), 1210(w), 1185(w), 1150(w), 1145(w), 1105(s), 1080(w), 1055(m), 1045(sh), 1015(w), 1005(m), 950(w), 915(w), 900(w), 890(w), 860(m), 825(m), 785(w), 680(s) cm$^{-1}$.

EXAMPLE 23

(trans-Dihydroxo)(β-chlorolactato-O,O')(exo,cis-bicyclo[2.2.1]heptane-2,3-diamine)platinum(IV) 50

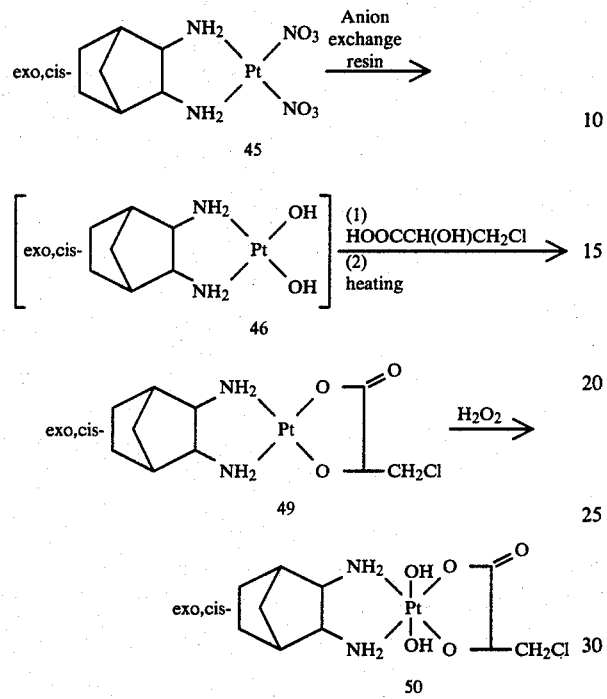

23-(1): Preparation of (β-chlorolactato-O,O')(exo,cis-bicyclo[2.2.1]heptane-2,3-diamine)platinum(II) 49

Chlorolactic acid (0.240 g, 1.93 mmol) was added to 60 ml of an aqueous solution of 2.0 mmol of the dihydroxo-compound 46 prepared in the same manner as in Example 22-(1).

The mixture was heated at 55° C. for 4 hours and concentrated. The residue was dissolved in methanol, purified by silica-gel column chromatography, and recrystallized from methaonol-acetone to give 0.33 g (yield: 37%) of the compound 49 as colorless crystals.

m.p.: 200° C.~(decomp.).

The compound 49 showed 2 spots on tlc (Rf values are 0.56 and 0.49 (developer: H$_2$O(1)-acetone(3)-methanol(12)), whereby the compound 49 seemed to be a mixture of α- and β-(β-chlorolactato-O,O')(exo, cis-bicyclo[2.2.1]heptane-2,3-diamine)platinum (II).

Anal. Calcd. (%) [for C$_{10}$H$_{17}$N$_2$O$_3$ClPt]:
C, 27.06; H, 3.86; N, 6.31; Cl, 7.99; Pt, 43.96. Found (%): C, 26.74; H, 4.11; N, 6.31; Cl, 7.96; Pt, 43.22.

IR: $\nu_{max}$(Nujol) 3500(w), 3400(w), 3200(m), 3100(m), 1640(s), 1350(m), 1280(w), 1265(w), 1180(w), 1145(w), 1095(m), 1050(w), 1030(w), 910(w), 880(w), 830(w) cm$^{-1}$.

$^1$HNMR: (in D$_2$O, ppm from TMS as external standard, δ): 1.0–1.6(m, 4H, C$_4$H$_2$C$_5$H$_2$), 1.36(br, 12 Hz, 1H, C$_7$anti H), 2.24(bs, 2H, C$_1$H, C$_4$H), 2.34, 2.60(2bd, 12Hz, C$_7$SynH), 2.84, 2.87(2s, 1.5 Hz, satellite J$_{195Pt-H}$=27 Hz, 2H, C$_2$H C$_3$H), 3.65–3.67(2d, 45 Hz, 2H, CH$_2$Cl), 4.22(t, 4.5 Hz, 1H, CHCH$_2$Cl).

23-(2): Preparation of the compound 50

The compound 49 (0.146 g, 0.329 mmol) was dissolved in 10 ml of water at 50° C. The mixture was cooled and 0.3 ml (0.882 mmol) of 10% aqueous hydrogen peroxide was added thereto. The resulting mixture was stirred for about 1 hour and the precipitating crystals were collected by filtration. The mother liquid was concentrated to give further crystals. The crystals provided above were combined, washed with a small amout of water, and dried under reduced pressure to give 0.082 g (yield: 50.5%) the compound 50 monohydrate.

m.p.: 189° C.~(decomp.).

Anal. Calcd. (%) [for C$_{10}$H$_{19}$N$_2$O$_5$ClPt(H$_2$O)$_{1.0}$]: C, 24.22; H, 4.27; N, 5.65; Cl, 7.63; Pt, 39.35. Found (%): C, 24.20; H, 4.27; N, 5.80; Cl, 6.97; Pt, 39.88. IR: $\nu_{max}$(Nujol) 3525(m), 3420(br,m), 3170(s), 1675(vs), 1602(s), 1580(s), 1410(m), 1345(s), 1315(m), 1290(s), 1280(m), 1245(s), 1210(sh), 1180(w), 1160(w), 1090(s), 1050(m), 1040(m), 1015(m), 1000(w), 950(w), 920(sh), 905(m), 870(m), 820(m), 785(w), 730(w), 700(w), 675(m) cm$^{-1}$.

$^1$HNMR: (in D$_2$O, ppm from TMS as external standard, δ): 1.49–2.24(m, bicyclo[2.2.1]heptane 8H), 2.93–3.07(m, —NH$_2$—CH, 2H), 3.74–4.00(m, —CH$_2$Cl, 2H), 4.10–4.34(m, Pt—O—CH, 1H).

EXAMPLE 24

(trans-Dihydroxo)(glycolato-O,O')(adamantane-1,2-diammine)platinum(IV) 52

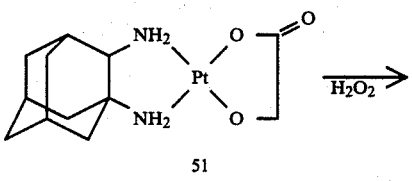

To an aqueous solution (4 ml) of 0.044 g (1.00 mmol) of (glycolato-O,O')(adamantane-1,2-diamine)platinum-(II) 51 [with proviso that 51 is a mixture of ab-(glycolato-O,O')-cd-(adamantane-1,2-diamine)-platinum(II) and ba-(glycolato-O,O')-cd-(adamantane-1,2-diamine)platinum(II)] was added 0.075 g of 10% aqueous hydrogen peroxide. The mixture was allowed to stand at room temperature for 1 hour and cooled. The resulting slightly yellowish crystals were collected by filtration, washed with a small amount of water, and dried at room temperature for a while to give 0.025 g of the compound 52 3 mol hydrate. [with proviso that 52 is a mixture of af-(dihydroxo)-bc-(glycolato-O,O')-de-(adamantane-1,2-diamine)platinum(IV) and af-(dihydroxo)-cb-(glycolato-O,O')-de-(adamantane-1,2-diamine)platinum(IV)].

Anal. Calcd. (%) [for C$_{12}$H$_{26}$N$_2$O$_6$Pt]: C, 29.44; H, 5.36; N, 5.72. Found (%): C, 29.11; H, 4.85; N, 5.84.

m.p.: gradually decomposed at 215° C.~.

IR: $\nu_{max}$(Nujol) 3540(sh), 3500(m), 3140(s), 1660(s), 1595(s), 1335(m), 1295(m), 1185(w), 1060(m), 980(w), 905(m), 760(m), 715(w) cm$^{-1}$.

EXAMPLE 25

(trans-Dihydroxo)(glycolato-O,O')bis(isopropylamine)-platinum(IV) 57

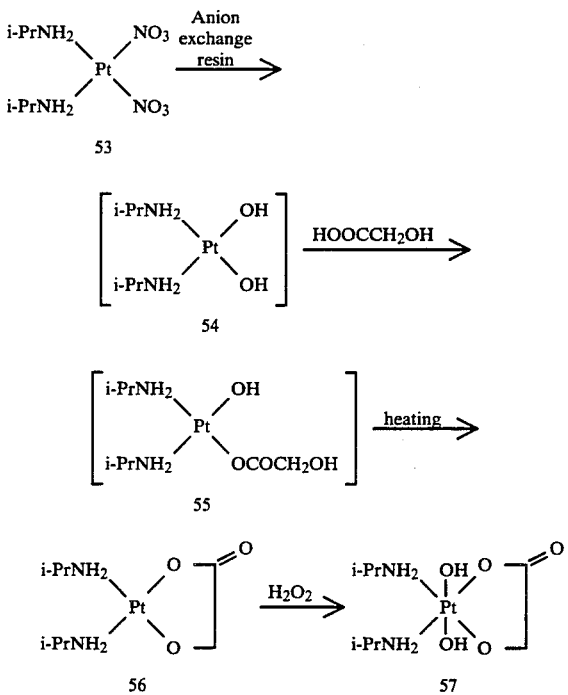

(wherein i-Pr is isopropyl)

25-(1) Preparation of (glycolato-O,O')bis(isopropylamino)-platinum(II) 56

A solution of 1.90 g (4.35 mmol) of (cis-dinitrato)bis-(isopropylamine(platinum(II)) (known compound JPN Unexamd. Pat. Pub. No. 54-70226) in 40 ml of water was passed through a column of Diaion SA-10A (OH type) to give an aqueous solution of (cis-dihydroxo)bis-(isopropylamine)platinum(II) 54. To the mixture were added 0.331 g (4.35 mmol) of glycolic acid and 0.860 g (8.60 mmol) of sodium glycolate.

The resulting mixture was concentrated to 45 ml and heated at 60° C. for 6 hours. The reaction mixture was concentrated to give 1.16 g (yield; 69%) of slightly yellowish crystalline compound 56.

m.p.: gradually decomposed at higher than 200° C.
Anal. Calcd. (%) [for $C_8H_{20}N_2O_3Pt$]: C, 24.81; H, 5.21; N, 7.23; Pt, 50.37 Found (%): C, 24.47; H, 5.06; N, 7.14; Pt, 50.64.

IR: $\nu_{max}$(Nujol) 3200(m), 3175(m), 3120(m), 1610(s), 1360(m), 1315(m), 1280(w), 1260(w), 1160(m), 1115(w), 1070(m), 940(w), 920(m), 820(w), 810(w), 750(w) cm$^{-1}$.

$^1$HNMR: (in $D_2O$, ppm from TMS as external standard, δ) 1.76(d, J=6.5 Hz, isopropyl $CH_3$), 3.33(bm, isopropyl CH), 4.52(s, $J_{195Pt-H}$=34 Hz, glycolato $CH_2$), 5.0(b, $NH_2$).

25-(2): Preparation of the compound 57

To a slution of 0.750 g (1.94 mmol) of the compound 56 provided above in 30 ml of water was added 1.5 g of 10% aqueous hydrogen peroxide. The mixture was allowed to stand at room temperature for 2 hours and concentrated. The residue was washed with acetone and with ether; and dried at room temperature under reduced pressure for a while to give 0.74 g (yield: 89%) of the compound 57 0.5 mol hydrate.

m.p.: gradually decomposed at 175° C.
water solubility: easy.
Anal. Calcd. (%) [for $C_8H_{22}N_2O_5Pt(H_2O)_{0.5}$]: C, 22.32; H, 5.39; N, 6.51; Pt, 45.32. Found (%): C, 22.16; H, 5.09; N, 6.44; Pt, 45.18.

IR: $\nu_{max}$(Nujol) 3475(m), 3400(sh), 3200(m), 3100(m), 1640(s), 1610(s), 1350(s), 1300(w), 1270(w), 1165(w), 1100(w), 1070(m), 970(w), 920(w), 820(w), 760(w) cm$^{-1}$.

$^1$HNMR: (in $D_2O$, ppm from TMS as external standard, δ) 1.72(d, J=6.3 Hz, isoprpyl $CH_3$), 1.75(d, J=6.3 Hz, isopropyl $CH_3$), 3.66(m, isopropyl CH), 4.70(s,satellite $J_{195Pt-H}$=23.0 Hz, glycolato $CH_2$).

EXAMPLE 26

(trans-Dichloro)(mandelato-O,O')(diammine)platinum-(IV) 58

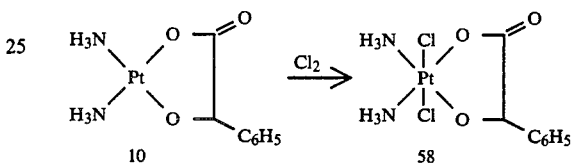

To a solution of 375 mg (1.0 mmol) of (mandelato-O,O') (diammine)platinum(II) 10 in 8 ml of water was added 30 ml of 0.28% aqueous chlorine (containing 1.17 mmol of chlorine). The mixture was allowed to stand at room temperature for 1.5 hours, concentrated at lower than 35° C. under reduced pressure, and the residue was dried in vacuo. This was dissolved in 5 ml of 70% ethanol and purified by passing through a silica-gel column [developer: $H_2O$-ethanol (2:5 v/v)]. The substance of which the Rf value on silica-gel tlc was 0.66 was collected, re-precipitated by water-ethanol, and washed with ether to give 350 mg (yield: 77%) of the compound 58.

m.p.: 190°–210° C.
Anal. Calcd. (%) [for $C_8H_{12}Cl_2N_2O_3Pt$]: C, 21.34; H, 2.69; N, 6.22; Pt, 43.33. Found (%): C, 21.33; H, 3.22; N, 5.91; Pt, 44.25.

IR: $\nu_{max}$(Nujol) 3600–3350(m,br), 3300–3000(m,br), 1660(s), 1590(sh), 1320(m), 1255(m), 1085(w), 1049(m), 1028(m), 953(m), 825(w), 760(m), 710(m), 680(w) cm$^{-1}$.

$^1$HNMR: (in $D_2O$, ppm from TMS as external standard, δ): 6.03(m, glycolato CH—), 7.96(s, —$C_6H_5$).

EXAMPLE 27

(trans-Dihydroxo)(isobutylglycolato-O,O')(diammine)-platinum(IV) 60

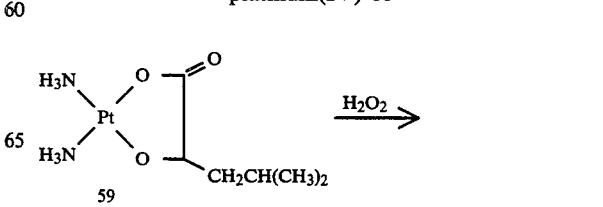

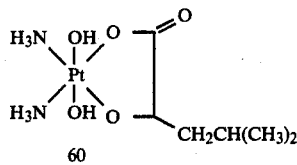

To a solution of 1.656 g (4.61 mmol) of (isobutyl-glycolato-O,O')(diammine)platinum(II) 59 in 10 ml of water was added about 4 ml (11.75 mmol) of 10% aqueous hydrogen peroxide at room temperature. The precipitating slightly yellowish crystals were collected by filtration, recrystallized from water, and dried at 45° C. in vacuo until the weight of the crystals was constant, whereby 774.7 g (yield: 42.7%) of the compound 60 was obtained.

m.p.: 170° C. ~(decomp.).

Ana. Calcd. (%) [for $C_6H_{18}N_2O_5Pt$]: C, 18.32; H, 4.61; N, 7.12; Pt, 49.60. Found (%): C, 18.12; H, 4.58; N, 7.11; Pt, 49.32.

IR: $\nu_{max}$(Nujol) 3400(sh), 3150(sh), 1600(s), 1350(sh), 1325(w), 1285(m), 1260(w), 1225(w), 1170(w), 1130(w), 1080(m), 935(m), 860(sh), 840(m), 795(w), 670(b) cm$^{-1}$.

$^1$HNMR: (in $D_2O$, ppm from TMS as external standard, δ) 1.38(d, —C(CH$_3$)$_2$J=7 Hz), 1.72–2.58(m, —CH$_3$—CH), 4.95(q, —O—CH=), Rf=0.44(silica-gel, H$_2$O(2)-ethanol(5)).

EXAMPLE 28

(trans-Dichloro)(lactato-O,O')(diammine)platinum(IV) 61

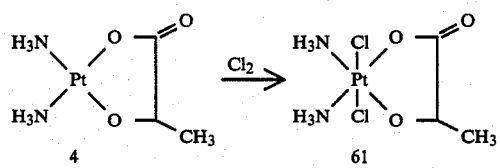

To a solution of 158 mg (0.50 mmol) of (lactato-O,O')(diammine)platinum(II) 4 in 2 ml of water was added 13 ml of 0.28% aqueous chlorine (containing 0.51 mmol of chlorine). The mixture was allowed to stand at room temperature for 2 hours, and the reaction mixture was neutralized with aqueous sodium hydroxide and dried up under reduced pressure to give yellow solid.

The yellow solid was purified by silica-gel chromatography [developer: methanol-acetone (4:1 v/v)] to give 105 mg of the compound 61 which contained 0.25 mol methanol as crystallization solvent.

m.p.: gradually decomposed at 185° C.~.

Anal. Calcd. (%) [for $C_3H_{10}N_2O_3Cl_2Pt(CH_3OH)_{0.25}$]: C, 9.86; H, 2.80; N, 7.07; Pt, 17.90. Found (%): C, 9.55; H, 2.91; N, 6.60; Pt, 17.44.

IR: $\nu_{max}$(Nujol) 3150(s), 1640(s), 1640(s), 1570(m), 1330(s), 1260(m), 1095(w), 1030(m), 860(w), 760(w) cm$^{-1}$.

$^1$HNMR: (in $D_2O$, ppm from TMS as external standard, δ) 1.85(d, lactato-CH$_3$), 3.83(s,methanol CH$_3$ as a solvent), 5.10(m,lactato CH).

EXAMPLE 29

(trans-Dichloro)(glycolato-O,O')(trans-l-cyclohexane-1,2-diamine)platinum(IV) 62

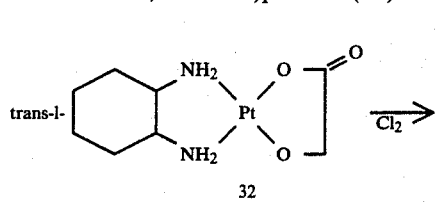

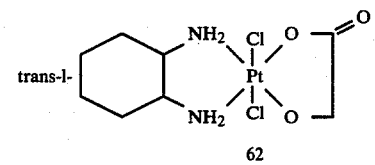

To a solution of 1.257 g (3.2 mmol) of (glycolato-O,O')(trans-l-cyclohexane-1,2-diamine)platinum(II) 32 0.5 mol hydrate in 26 ml of water was added 82.4 ml of 0.28% aqueous chlorine (containing 3.2 mmol of chlorine). The mixture was stirred at room temperature for 1 hour and the floating substance was removed by filtration.

The resulting mixture was neutralized with 1N sodium hydroxide, concentrated under reduced pressure, and cooled. The precipitating yellow crystalline material was collected by filtration and dried in vacuo until the weight of the material was constant whereby 683 mg (yield: 45.1%) of the compound 62 was obtained.

m.p.: gradually decomposed at 177° C.~.

Anal. Calcd. (%) [for $C_8H_{16}N_2O_3Cl_2Pt.H_2O$]: C, 20.35; H, 3.84; N, 5.93; Cl, 15.01; Pt, 41.31. Found (%): C, 20.24; H, 3.75; N, 5.98; Cl, 14.88; Pt, 42.92.

IR: $\nu_{max}$(Nujol) 3230(w), 3155(m,br), 3060(m,br), 1690(sh), 1660(s), 1590(m), 1570(sh), 1540(sh), 1410(w), 1322(w), 1280(s), 1270(sh), 1240(sh), 1210(w), 1177(m), 1135(w), 1060(sh), 1045(m), 1017(m), 905(m), 890(w), 860(w), 840(w), 760(m) cm$^{-1}$.

$^1$HNMR: (in $D_2O$, ppm from TMS as external standard, δ): 1.42–2.27, 2.40–2.86(b, cyclohexyl-CH$_2$—8H), 3.10–3.54(b, —N—CH—), 4.67(s, satellite, $J_{195Pt-H}$=18 Hz).

What we claim is:

1. A compound of the formula:

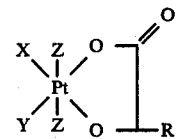

wherein R is hydrogen, phenyl, or lower alkyl optionally substituted by the group consisting of hydroxy and halogen; X and Y each is amine or lower alkylamine; or X and Y taken together form ethane-1,2-diamine, cyclohexane-1,2-diamine, bicyclo[2.2.1]heptane-2,3-diamine, adamantane-1,2-diamine, cyclohexane-1,1-bis(methylamine), or cyclohexane-2-amine-1-methylamine; and Z is halogen, hydroxy, or an alkali-metal salt of hydroxy.

2. A compound claimed in claim 1, wherein R is hydrogen, phenyl, hydroxy-lower alkyl, or halogeno-lower alkyl.

3. A compound claimed in claim 1, namely (trans-dihydroxo)-(glycolato-O,O')(diammine)platinum(IV).

4. A compound claimed in claim 1, namely (trans-dichloro)-(glycolato-O,O')(diammine)platinum(IV).

5. A compound claimed in claim 1, namely (trans-dihydroxo)-(lactato-O,O')(diammine)platinum(IV).

6. A compound claimed in claim 1, namely (trans-dihydroxo)-(β-chlorolactato-O,O')(diammine)platinum(IV).

7. A compound claimed in claim 1, namely (trans-dihydroxo)-(mandelato-O,O')(diammine)platinum(IV).

8. A compound claimed in claim 1, namely (trans-dihydroxo)-(glycolato-O,O')bis(methylamine)platinum(IV).

9. A compound claimed in claim 1, namely (trans-dichloro)-(glycolato-O,O')bis(methylamine)platinum(IV).

10. A compound claimed in claim 1, namely (trans-dihydroxo)-(glycolato-O,O')(ethane-1,2-diamine)-platinum(IV).

11. A compound claimed in claim 1, namely (trans-dihydroxo)-(glycolato-O,O')(cis-cyclohexane-1,2-diamine)platinum(IV).

12. A compound claimed in claim 1, namely (trans-dihydroxo)-(glycolato-O,O')(trans-l-cyclohexane-1,2-diamine)platinum(IV).

13. A compound claimed in claim 1, namely (trans-dihydroxo)-(glycolato-O,O')bis(isopropylamine)-platinum(IV).

14. A compound claimed in claim 1, namely (trans-dichloro)-(glycolato-O,O')(trans-l-cyclohexane-1,2-diamine)platinum(IV).

15. An antibacterial composition comprising an effective amount of a compound of claim 1 and one or more pharmaceutically acceptable carriers.

* * * * *